US008063205B2

(12) United States Patent
Hara et al.

(10) Patent No.: US 8,063,205 B2
(45) Date of Patent: Nov. 22, 2011

(54) METHOD FOR PRODUCING 2-OXAZOLINE ANALOGUE OR 1,3-OXAZINE ANALOGUE

(75) Inventors: Shoji Hara, Hokkaido (JP); Tsuyoshi Fukuhara, Hokkaido (JP); Toshio Hidaka, Ibaraki (JP)

(73) Assignees: National University Corporation Hokkaido University, Hokkaido (JP); Mitsubishi Gas Chemical Company, Inc., Tokyo (JP)

( * ) Notice: Subject to any disclaimer, the term of this patent is extended or adjusted under 35 U.S.C. 154(b) by 700 days.

(21) Appl. No.: 12/065,347

(22) PCT Filed: Aug. 30, 2006

(86) PCT No.: PCT/JP2006/317086
§ 371 (c)(1),
(2), (4) Date: Feb. 29, 2008

(87) PCT Pub. No.: WO2007/026753
PCT Pub. Date: Mar. 8, 2007

(65) Prior Publication Data
US 2009/0281309 A1     Nov. 12, 2009

(30) Foreign Application Priority Data
Sep. 1, 2005   (JP) .................... 2005-254041

(51) Int. Cl.
C07D 263/12  (2006.01)
C07D 263/16  (2006.01)
C07D 263/56  (2006.01)
C07D 265/08  (2006.01)
C07D 277/10  (2006.01)
C07D 279/06  (2006.01)

(52) U.S. Cl. ............ 544/53; 544/88; 548/146; 548/215

(58) Field of Classification Search .................. 544/53, 544/88; 548/146, 215
See application file for complete search history.

(56) References Cited

U.S. PATENT DOCUMENTS
4,661,599 A   4/1987  Palla et al.
2004/0073065 A1   4/2004  Hidaka et al.

FOREIGN PATENT DOCUMENTS
DE   2158615        11/1971
GB   1 417 411      12/1975
JP   55-066569      5/1980
JP   60-226865      11/1985
JP   2006-160709    6/2006

OTHER PUBLICATIONS

Akio Takaoka et al., "Alchohol oyobi carboxylic acid no Fussokazai to shite no hexafluoropentene-dialkylamine adduct no Yukoriyo—tetrafluoroethyl—substituted benzo-fused heterocylclic compound and fluorocytosine derivative no Gosei-", Journal of the Chemical Society of Japan, 1985, No. 11, pp. 2161-2168.

Takaoka et al., "Preperation of bensoheterocycles containing a chlorofluoromethyl group using the yarovenko reagent", Journal of Fluorine Chemistry, 1979, vol. 14, No. 5, pp. 421-428.

Extended European Search Report, including Supplementary European Search Report and European Search Opinion, dated Feb. 17, 2010, for Application No. EP 06 79 7059.

T. Nomoto, et al., "Synthesis of (Fluoroalkyl)amines by Deoxyfluorination of Amino Alcohols", *SYNLETT*, No. 11, 2006, pp. 1744-1746.

E. D. Bergmann, et al., "Organic Fluorine Compounds, Part 43*, Applications of (1,1,2-Trifluoro-2-Chloroethyl)-Diethylamine as Fluorinating Agent", *Israel Journal of Chemistry*, vol. 8, 1970, pp. 925-933.

*Primary Examiner* — Venkataraman Balasubramanian

(74) *Attorney, Agent, or Firm* — Antonelli, Terry, Stout & Kraus, LLP.

(57) ABSTRACT

The present invention is a method for producing a 2-oxazoline analogue or a 1,3-oxazine analogue represented by the following general formula (3) by reacting a 1,2-aminoalcohol compound or a 1,2-aminothiol compound with an α,α-dihaloamine compound.

(In the formula, n represents 0 or 1, and R represents an oxygen atom or a sulfur atom. $R^1$, $R^2$ and $R^3$ each represents an atom or a group shown in Group 1 to Group 3, and $R^0$ represents an atom or a group shown in Group 2 or Group 3. Two or more of $R^1$, $R^2$ and $R^3$ may be bonded to each other to form a ring.

Group 1: a hydrogen atom, a halogen atom, a nitro group, a cyano group, a formyl group, a carboxyl group, a sulfonyl group, a sulfinoyl group or a sulfenyl group;

Group 2: an alkyl group, which may have an arbitrary substituent, an aryl group or an aralkyl group; and Group 3: an alkyl-substituted, aryl-substituted or aralkyl-substituted oxy group, a carbonyl group, an oxycarbonyl group, a carbonyloxy group, a thio group, a sulfonyl group, a sulfinoyl group or a sulfenyl group)

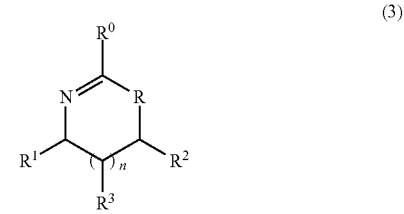

(3)

5 Claims, No Drawings

METHOD FOR PRODUCING 2-OXAZOLINE ANALOGUE OR 1,3-OXAZINE ANALOGUE

TECHNICAL FIELD

The present invention relates to a novel method for producing a 2-oxazoline analogue or a 1,3-oxazine analogue, i.e., a 2-oxazoline compound, a 2-thiazoline compound, a 1,3-oxazine compound or a 1,3-thiazine compound. More specifically, the present invention relates to a method for producing a 2-oxazoline analogue or a 1,3-oxazine analogue, such as a 2-oxazoline compound, a 5,6-dihydro-4H-1,3-oxazine compound, a 2-thazoline compound and a 5,6-dihydro-4H-1,3-thiazine compound, having broad usages including medicines, agrochemicals, optical recording materials and the like, from an aminoalcohol or aminothiol compound and an $\alpha,\alpha$-dihaloamine under mild conditions in a simple manner.

BACKGROUND ART

An oxazoline analogue and an oxazine analogue have broad usages including medicines, agrochemicals, optical recording materials and the like, and anticancer activity and diabetes treatment effect of an oxazoline derivative receive attention in recent years.

Various synthesis methods for an oxazoline compound have been known. An oxazoline ring has three regioisomers, and among these, a synthesis method for a 2-oxazoline compound has been best known.

Typical production methods for a 2-oxazoline compound include (1) a method of reacting an alkali, triethylamine, acetic anhydride or ethyl orthoformate to an N-(2-haloethyl) carboxylic amide derivative, (2) a method of subjecting N-(2-hydroxyethyl) carboxylic amide to dehydration ring-closing reaction by heating with concentrated sulfuric acid or thionyl chloride, (3) a method of heating a carboxylic acid and 2-aminoethanol along with an alumina catalyst, (4) a method of heating a nitrile compound and 2-aminoethanol in the presence of a strong base, such as sodium methoxide and the like, or by using calcium chloride as a base, (5) a method of heating an acid imide ester and 2-aminoethanol along with alumina, or acting an alkali or sulfuric acid to an imino ester of 2-haloethanol, and (6) a method of heating an acyl derivative of an unsaturated amine with a mineral acid, such as sulfuric acid, hydrochloric acid or the like. Various modified methods can be considered for the aforementioned methods, and other raw materials may be used. For example, in the methods (1) and (2), a thiocarboxylic acid amide can be used instead of an acid amide, and a 2-thiazoline compound is obtained in this case.

The methods (1) to (6) will be described more specifically. For example, as the method (1), potassium hydroxide or acetic anhydride is reacted to 2-chloroethylformamide to provide 2-oxazoline, and the case where 2-bromoethylbenzamide is used provides 2-phenyl-2-oxazoline (see, for example Non-patent Document 1). As the method (2), thionyl chloride is reacted to 2-formamide ethanol to provide 2-oxazoline, and N-(2-hydroxyethyl)benzamide is heated with phosphorous pentoxide to provide 2-phenyl-2-oxazoline (see, for example, Non-patent Document 2). As the method (3), benzoic acid and 2-aminoethanol are heated with alumina to provide 2-phenyl-2-oxazoline (see, for example, Non-patent Document 3). As the method (4), benzonitrile and 2-aminoethanol are heated with calcium chloride at 110 to 120° C. to provide 2-phenyl-2-oxazoline (see, for example, Non-patent Document 4 and Patent Document 1). As the method (5), methyl benzimidate and 2-aminoethanol are heated with alumina to provide 2-phenyl-2-oxazoline (see, for example, Non-patent Document 5). Vinylbenzamide is simply heated to provide 2-phenyl-2-oxazoline. As the method (6), N-allylbenzamide is heated with sulfuric acid to provide 5-methyl-2-phenyl-2-oxazoline (see, for example, Non-patent Document 6).

Accordingly, various kinds of 2-oxazoline compounds can be conventionally produced, and a 2-oxazoline compound having an intended substituent can be produced by selecting a reactant having a suitable substituent. For example, reaction of a 1,2-substituted 2-aminoethanol and a carboxylic acid compound or a nitrile compound can be considered. However, there are often cases where completely no reaction proceeds or cases where severe reaction conditions are needed and unfavorable reaction results are provided, depending on the substituent. Accordingly, there is difficulty in synthesis of a compound having substituents on the 2-, 4- and 5-positions of an oxazoline ring, and it is necessary to provide another measure different from the conventional ones for obtaining a 2-oxazoline compound having an intended substituent.

There are the similar situations for a thiazoline compound, an oxazine compound, a thiazine compound and the like, which are analogue compounds thereof. Specifically, there is no versatile method found for synthesizing an oxazoline analogue or an oxazine analogue having an arbitrary substituent under mild conditions, and a simple synthesis method is being demanded.

Non-patent Document 1: Gabriel Heymann, Chem. Ber., 23, 1890, 2502

Non-patent Document 2: Wenker, J. Am. Chem. Soc., 57, 1935, 1079

Non-patent Document 3: W. Seeliger, Angev. Chem. GE, 78, 20, 1966, 913-927

Non-patent Document 4: W. O, Siegel, J. Org. Chem., EN, 42, 11, 1977, 1872-1877

Non-patent Document 5: Boualem Oussaid, et al., Synth. Commun., EN, 25, 5, 1995, 659-666

Non-patent Document 6: S. Gabriel, R. Stelzner, Chem. Ber., 28, 1895, 2929

Patent Document 1: German Patent No. 2,158,615

DISCLOSURE OF THE INVENTION

An object of the present invention is to provide a method for producing, under mild conditions in a simple manner, a 2-oxazoline analogue or a 1,3-oxazine analogue, such as a 2-oxazoline compound or a 2-thiazoline compound, which may have a substituent at the 2-, 4- and 5-positions, and a 5,6-dihydro-4H-1,3-oxazine compound or a 5,6-dihydro-4H-1,3-thiazine compound, which may have a substituent at the 2-, 4-, 5- and 6-positions.

As a result of earnest investigations made by the inventors for solving the problem, it has been found that a 2,4,5-substituted 2-oxazoline compound can be easily obtained under mild conditions from a 1,2-substituted 2-aminoalcohol compound and an $\alpha,\alpha$-dihaloamine by a versatile method capable of being applied irrespective of the substituents, and a 2,4,5,6-substituted 5,6-dihydro-4H-1,3-oxazine compound can be obtained from a 1,2,3-substituted 3-aminoalcohol compound, and found similarly that a 2,4,5-substituted 2-thioazoline compound can be obtained from a 1,2-substituted 2-aminothiol compound, and a 2,4,5,6-substituted 5,6-dihydro-4H-1,3-thiazine compound can be obtained from a 1,2,3-substituted aminothiol compound, and thus the present invention has been completed.

In the above description, the 1,2-substituted 2-aminoalcohol compound means a 2-aminoalcohol compound that may have a substituent at the 1- or 2-position, and the 2,4,5-substituted 2-oxazoline compound means a 2-oxazoline compound that may have a substituent at least one position of the 2-, 4- and 5-positions, the same rules are being applied to the others.

That is, the present invention relates to a method for producing a 2-oxazoline analogue or a 1,3-oxazine analogue shown in the items 1 to 6 below.

1. A method for producing a 2-oxazoline analogue or a 1,3-oxazine analogue represented by the general formula (3) comprising reacting an amino compound represented by the general formula (1) with an α,α-dihaloamine represented by the general formula (2).

[ka 1]

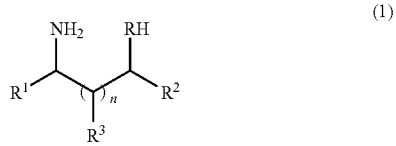

(1)

[ka 2]

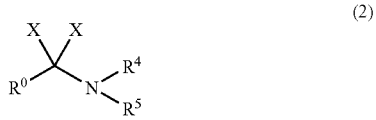

(2)

[ka 3]

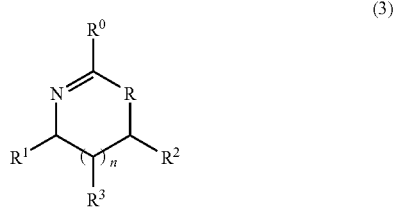

(3)

(In the formulae, in the general formula (1) and the general formula (3), n represents 0 or 1, and R represents an oxygen atom or a sulfur atom. In the general formula (2), X represents a fluorine atom, a chlorine atom, a bromine atom or an iodine atom. In the general formulae (1), (2) and (3), $R^1$, $R^2$, $R^3$, $R^4$ and $R^5$ each represents an atom or a group shown in Group 1 to Group 3 below, and in the general formulae (2) and (3), $R^0$ represents an atom or a group shown in Group 2 or Group 3 below.

Group 1: a hydrogen atom, a halogen atom, a nitro group, a cyano group, a formyl group, a carboxyl group, a sulfonyl group, a sulfinoyl group or a sulfenyl group;

Group 2: an alkyl group, an aryl group or an aralkyl group, which may have an arbitrary substituent; and Group 3: an alkyl-substituted, aryl-substituted or aralkyl-substituted oxy group, a carbonyl group, an oxycarbonyl group, a carbonyloxy group, a thio group, a sulfonyl group, a sulfinoyl group or a sulfenyl group;

$R^0$, $R^1$, $R^2$, $R^3$, $R^4$ and $R^5$ each may be the same as or different from each other. Two or more of $R^1$, $R^2$ and $R^3$ or two or more of $R^0$, $R^4$ and $R^5$ may be bonded to each other to form a ring.)

2. The method for producing a 2-oxazoline analogue or a 1,3-oxazine analogue of the item 1, wherein in the α,α-dihaloamine represented by the general formula (2), $R^0$ represents a phenyl group, a 2-methylphenyl group, a 3-methylphenyl group, a 4-methylphenyl group, a 2-methoxyphenyl group or a 4-methoxyphenyl group, $R^4$ and $R^5$ each represents an alkyl group having 24 or less carbon atoms, an aryl group or an aralkyl group, and X represents a fluorine atom.

3. The method for producing a 2-oxazoline analogue or a 1,3-oxazine analogue of the item 1 or 2, wherein a 2-oxazoline compound represented by the general formula (3), wherein n represents 0, and R represents an oxygen atom, is produced by reacting an aminoalcohol represented by the general formula (1), wherein n represents 0, and R represents an oxygen atom, with an α,α-dihaloamine represented by the general formula (2).

4. The method for producing a 2-oxazoline analogue or a 1,3-oxazine analogue of the item 1 or 2, wherein a 1,3-oxazine compound represented by the general formula (3), wherein n represents 1, and R represents an oxygen atom, is produced by reacting an aminoalcohol represented by the general formula (1), wherein n represents 1, and R represents an oxygen atom, with an α,α-dihaloamine represented by the general formula (2).

5. The method for producing a 2-oxazoline analogue or a 1,3-oxazine analogue of the item 1 or 2, wherein a 2-thiazoline compound represented by the general formula (3), wherein n represents 0, and R represents a sulfur atom, is produced by reacting an aminothiol represented by the general formula (1), wherein n represents 0, and R represents a sulfur atom, with an α,α-dihaloamine represented by the general formula (2).

6. The method for producing a 2-oxazoline analogue or a 1,3-oxazine analogue of the item 1 or 2, wherein a 5,6-dihydro-4H-1,3-thiazine compound represented by the general formula (3), wherein n represents 1, and R represents a sulfur atom, is produced by reacting a thiol represented by the general formula (1), wherein n represents 1, and R represents a sulfur atom, with an α,α-dihaloamine represented by the general formula (2).

BEST MODE FOR CARRYING OUT THE INVENTION

In the present invention, the 2-oxazoline analogue means a 2-oxazoline compound and a 2-thiazoline compound, and the 1,3-oxazine analogue means a 5,6-dihydro-4H-1,3-oxazine compound and a 5,6-dihydro-4H-1,3-thiazine compound.

In the present invention, a 2-oxazoline compound or a 2-thiazoline compound having an intended substituent can be produced from a 1,2-substituted 2-aminoalcohol compound or a 1,2-substituted 2-aminothiol compound having various substituents and an α,α-dihaloamine compound under mild conditions in a simple and highly versatile manner. Similarly, in the case where a 1,2,3-substituted 3-aminoalcohol compound is used as a raw material, a 5,6-dihydro-4H-1,3-oxazine compound can be obtained, and a 5,6-dihydro-4H-1,3-thiazine compound can be obtained from a 1,2,3-substituted 3-aminothiol compound.

The amino compound used as a raw material in the present invention is a 1,2-substituted 2-aminoalcohol compound, a 1,2-substituted 2-aminothiol, a 1,2,3-substituted 3-aminoalcohol compound and a 1,2,3-substituted 3-aminothiol compound, which are racemic or optically active and may have a substituent, represented by the general formula (1).

A secondary aminoalcohol or aminothiol other than the general formula (1) may be used for the reaction of an α,α-dihaloamine above. For example, reaction of an amide alcohol and an α,α-dihaloamine produces a 2-oxazoline compound. More specifically, reaction of ethyl (2S,3R)-2-benzamide-3-hydroxybutyrate and N,N-diethyl-α,α-difluoro(3-methyl)benzylamine produces ethyl (4S,5S)-5-methyl-2-phenyl-2-oxazoline-4-carboxylate. In general, a 2,4,5-substituted 2-oxazoline is obtained from a 1,2-substituted 2-aminoalcohol, and a 2,4,5,6-substituted 5,6-dihydro-4H-1,3-oxazine is obtained from a 1,2,3-substituted 3-aminoalcohol. It has been found that a 2,4,5-substituted 2-thiazoline compound is obtained from a 1,2-substituted 2-aminothiol compound, and a 2,4,5,6-substituted 5,6-dihydro-4H-1,3-thiazine compound is obtained from a 1,2,3-substituted 3-aminothiol compound, and thus, the present invention has been completed.

In the general formula (1), n represents 0 or 1, and R represents an oxygen or sulfur atom. Substituents $R^1$, $R^2$ and $R^3$ may be anyone of hydrogen, halogen, a nitro group, a cyano group, a formyl group, a carboxyl group, a sulfonyl group, a sulfinoyl group and a sulfenyl group of Group 1, an alkyl group, an aryl group and an aralkyl group of Group 2, and an alkyl-substituted, aryl-substituted or aralkyl-substituted oxy group, a carbonyl group, an oxycarbonyl group, a carbonyloxy group, a thio group, a sulfonyl group, a sulfinoyl group and a sulfenyl group of Group 3. Two or more of $R^1$, $R^2$ and $R^3$ may be bonded to each other to form a ring. Examples of a compound having the ring formed by bonding include 2-aminophenol.

Accordingly, the amino compound of the general formula (1) includes a linear or branched aliphatic amino compound, which may have an aromatic ring, a heterocyclic ring, an alicyclic ring or an unsaturated group. The alkyl group, the aryl group and the aralkyl group are preferably those having 24 or less carbon atoms and may have a functional group.

Examples of the alkyl group of Group 2 for the substituents $R^1$, $R^2$ and $R^3$ include methyl, ethyl, propyl, isopropyl, butyl, isobutyl, t-butyl, n-pentyl, 1-methylbutyl, 2-methylbutyl, neopentyl, 1,1-dimethylpropyl, 1,2-dimethylpropyl, 1,3-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-3-methylpropyl, n-heptyl, n-octyl, 2-ethylhexyl, n-nonyl, n-decyl, n-dodecyl, cyclohexyl, decalyl, norbornyl, bicyclohexyl, adamantyl, menthyl and isomers thereof, and also include hydroxymethyl, hydroxyethyl, hydroxypropyl, hydroxybutyl, hydroxyphenyl, cyclohexyloxy and the like. Examples thereof also include an alkyl group partially containing an unsaturated bond, such as 1,2-ethylene, 1,3-propylene, 1,4-butylene, 1,5-pentylene, 1,6-hexylene, 1,2-cyclopentylene, 1,2-cyclohexylene and the like.

Examples of the aryl group include phenyl, o-tolyl, m-tolyl, p-tolyl, dimethylphenyl, naphthyl, fluorenyl, anthryl, phenanthryl and a positional isomer thereof, cumyl, mesityl, trimethylphenyl, hydroxyphenyl, methoxyphenyl and a positional isomer thereof, naphthyl, methylnaphthyl, dimethylnaphthyl, hydroxynaphthyl, biphenyl, tetralyl, t-phenyl and the like, and examples of an aryl group containing a hetero atom include furanyl, oxazolyl, pyridinyl, quinolyl, isoquinolyl, benzofranyl, dibenzofranyl, benzothienyl, chromenyl, indoyl and the like.

Examples of the aralkyl group include a benzyl group, a phenethyl group, a naphthylmethyl group, a naphtylethyl group and the like.

The alkyl group, the aryl group and the aralkyl group may contain a functional group, such as a hydroxyl group, halogen, a nitro group, a mercapto group, an amino group, an amide group, a cyano group, a carbonyl group, a carboxyl group, an acetyl group, an acyl group, an alkoxy group and a sulfonyl group, or other atoms or atomic groups. Examples of the aryl group containing other atoms or atomic groups include an alkoxy group, and examples thereof include methoxy, ethoxy, n-propoxy, isopropoxy, n-butoxy, t-butoxy, n-pentoxy, 1-methylbutoxy, 2-methylbutoxy, 3-methylbutoxy, neopentoxy, 1-ethylpropoxy, cyclopentoxy, n-hexoxy, cyclohexoxy, n-heptoxy, n-octoxy, n-decoxy, n-dodecoxy, menthoxy, isomers thereof, adamantyloxy and the like. Examples thereof also include 2-pyridyl, 3-pyridyl, 4-pyridyl, 2-quinolyl, 3-quinolyl, 4-quinolyl, alkyl-substituted groups thereof, halogen-substituted groups thereof, and the like. Examples thereof also include fluoroalkyl and fluoroaryl obtained by substituting a part of the alkyl groups, the aryl groups and the like mentioned above with fluorine, and trifluoromethylalkyl, trifluoromethylaryl and the like obtained by substituting them with a trifluoromethyl group.

The aminoalcohol compound represented by the general formula (1) wherein R represents an oxygen atom cannot be completely mentioned since it includes a wide range of compounds, and specific examples thereof include 2-aminoethanol, 3-aminopropan-1-ol, 1-aminopropan-2-ol, (R)-1-aminopropan-2-ol, (S)-1-aminopropan-2-ol, 2-aminopropan-1-ol, (R)-2-aminopropan-1-ol, (S)-2-aminopropan-1-ol (L-alaninol), 2-amino-2-methylpropan-1-ol, 2-amino-1-methylpropan-1-ol, (R)-2-amino-1-butan-1-ol, (S)-2-amino-1-butan-1-ol, (R)-2-amino-3-methylbutan-1-ol (D-valinol), L-valinol, (S)-2-amino-3,3-dimethylbutan-1-ol (L-t-leucinol), (2S)-2-amino-4-methylpentan-1-ol, (2S,3S)-2-amino-3-methylpentan-1-ol (L-isoleucinol), (S)-2-amino-4-methylpentan-1-ol (L-leucinol), (S)-2-amino-4-(methylthio)butan-1-ol (L-methioninol), (2R)-2-amino-3-phenylpropan-1-ol (D-phenylalaninol), L-phenylalaninol, (S)-2-amino-3-(1H-indol-3-yl)propan-1-ol (L-tryptophanol), (1R,2R)-2-amino-1-phenyl-1,3-propanediol, (1S,2S)-2-amino-1-phenyl-1,3-propanediol, (1R,2S)-2-amino-1,2-diphenylethanol, (1S,2R)-2-amino-1,2-diphenylethanol, 2-amino-2-phenylethanol, ethyl (2S,3R)-2-amino-3-hydroxybutyrate, 2-aminophenol, 3-aminophenol and the like.

Specific examples of the aminothiol compound represented by the general formula (1) wherein R represents a sulfur atom include compounds obtained by substituting the oxygen atom in the aminoalcohol compounds mentioned above with a sulfur atom.

The α,α-dihaloamine, which is used for reaction with the aminoalcohol compound or the aminothiol compound represented by the general formula (1), is represented by the general formula (2).

In the general formula (2), $R^4$ and $R^5$ may be, as similar to $R^1$, $R^2$ and $R^3$ mentioned above, any of hydrogen, halogen, a nitro group, a cyano group, a formyl group, a carboxyl group, a sulfonyl group, a sulfinoyl group and a sulfenyl group of Group 1. $R^0$, $R^4$ and $R^5$ may be anyone of an alkyl group, an aryl group and an aralkyl group of Group 2, and an alkyl-substituted, aryl-substituted or aralkyl-substituted oxy group, a carbonyl group, an oxycarbonyl group, a carbonyloxy group, a thio group, a sulfonyl group, a sulfinoyl group and a sulfenyl group of Group 3. Two or more of $R^0$, $R^4$ and $R^5$ may be bonded to each other to form a ring.

In the general formula (2), X represents a halogen atom, i.e., may be anyone of fluorine, chlorine, bromine and iodine atoms, and is particularly preferably a fluorine atom. Examples of the α,α-dihaloamine represented by the general formula (2) include linear or branched aliphatic compounds or the like, which may have an aromatic ring, a heterocyclic ring, an alicyclic ring or an unsaturated group, and $R^4$ and $R^5$ preferably have 24 or less carbon atoms. $R^4$ and $R^5$ may contain a functional group as similar to $R^1$, $R^2$ and $R^3$.

Examples of the alkyl group, the aryl group and the aralkyl group of Group 2 in the general formula (2) include compounds similar to those for the general formula (1).

Examples obtained by bonding two or more of $R^0$, $R^4$ and $R^5$ include pyrrolidin-1-yl, 3-methylimidazolidin-1-yl, 1,3-dimethylimidazolidin-2-ylidene, 2-morpholin-4-yl, N-piperidinyl, 4-methylpiperadin-1-yl and the like.

Specific example compounds of the α,α-dihaloamine represented by the general formula (2) includes the following compounds. That is, the examples includes difluoro-N,N-dimethylmethanamine, difluoro-N,N-diethylmethanamine, difluoro-N,N-di(n-propyl)methanamine, difluoro-N,N-di(isopropyl)methanamine, difluoro-N,N,-di(n-butyl)methanamine, difluoro-N,N-dipentylmethanamine, 1,1-difluoro-N,N-dimethylethanamine, 1,1-difluoro-N,N-diethylethanamine, 1,1-difluoro-N,N-di(n-propyl)ethanamine, 1,1-difluoro-N,N-di(isopropyl)ethanamine, 1,1-difluoro-N,N,-di(n-butyl)ethanamine, 1,1-difluoro-N,N-di(isobutyl)ethanamine, 2,2-difluoro-N,N-dimethylpropan-1-amine, 1,1,2,2,2-pentafluoro-N,N-dimethylethanamine, 1,1,2,2,2-pentafluoro-N,N-diethylethanamine, 1-cyano-1,1-difluoro-N,N-dimethylmethanamine, cyclopropyldifluoro-N,N,-dimethylmethanamine, cyclopropyldifluoro-N,N-diethylmethanamine, difluoro-N,N-dimethyl(phenyl)methanamine, difluoro-N,N-diethyl(phenyl)methanamine, 1,1-difluoro-N,N-dimethylbutan-1-amin-3-one, 1,1-difluoro-N,N-diethylbutan-1-amin-3-one, 2,2-dichloro-1,1-difluoro-N,N-dimethylbutan-1-amin-3-one, 1,1-difluoro-N,N-dimethyl-2-phenoxyethanamine, N,N-diethyl-1,1-difluoropropan-1-amine, N,N-diethyl-1,1-difluorobutan-1-amine, N,N-bis(2-hydroxymethyl)-1,1-difluorododecan-1-amine, N,N-bis(aminoethyl)-1,1-difluoro-2-methyl-2-propen-1-amine, N,N-diethyl-1,1-difluoro-2-(naphthyl-1-yloxy)-propan-1-amine, (N-(decahydronaphthalen-1-yl)difluoromethyl)-N-ethylethanamine, difluoro-N-methylmethanamine, 1,1-difluoro-N-methylethanamine, N-(difluoromethyl)-N-methylbenzenamine, 1,1-difluoro-N,N-dimethylbutan-1-amine, 1,1-difluoro-N,N,2-trimethylpropan-1-amine, N,N-diethyl-1,1-difluoro-2-methylpropan-1-amine, N,N-dimethyl-1,1-difluoropentan-1-amine, difluoro-N,N-dimethyl(phenyl)methanamine, N-(difluoro(phenyl)methyl)-N-ethylethanamine, N-(difluoro(m-tolyl)methyl)-N-ethylethanamine, N-(difluoro(o-tolyl)methyl)-N-ethylethanamine, N-(difluoro(p-tolyl)methyl)-N-ethylethanamine, 2,4-(dimethylphenyl)difluoro-N,N-dimethylmethanamine, 2,4-(dimethylphenyl)difluoro-N,N-diethylmethanamine, 2,6-(dimethylphenyl)difluoro-N,N-dimethylmethanamine, 2,6-(dimethylphenyl)difluoro-N,N-diethylmethanamine, N-(aminoethyl)-N-(1,1-difluoro-2-methylallyl)methandiamine, (E)-1,1-difluoro-N,N-dimethyl-3-prop-2-en-1-amine, difluoro(tetrahydrofuran-2-yl)-N,N-dimethylmethanamine, difluoro(tetrahydrofran-3-yl)-N,N-dimethylmethanamine, N-(difluoro(2-methoxyphenyl)methyl)-N-ethylethanamine, (4-chlorophenyl)difluoro-N,N-dimethylmethanamine, (4-bromophenyl)difluoro-N,N-dimethylmethanamine, (4-fluorophenyl)difluoro-N,N-dimethylmethanamine, N-(difluoro(mesityl)methyl)-N-ethylethanamine, difluoro-N,N-diethyl(naphthalen-2-yl)methanamine, difluoro(4-biphenyl)-N,N-diethylmethanamine, anthracen-2-yldifluoro-N,N-diethylmethanamine, cyclohexyldifluoro-N,N-diethylmethanamine, N,N-dimethyl-1,1-difluorodecan-1-amine, N,N-diethyl-1,1-difluorodecan-1-amine, difluoro-N,N-dimethyl(pyridin-2-yl)methanamine, difluoro-N,N-diethyl(pyridin-2-yl)methanamine, 2,2-difluoro-1,3-imidazolidine, 1-(difluoro(phenyl)methyl)piperidine, 4-(difluoro(phenyl)methyl)morpholine and the like.

The reaction of the aminoalcohol compound or the aminothiol compound represented by the general formula (1) and the α,α-dihaloamine represented by the general formula (2) can be carried out batch-wise, semi-batch-wise or continuously, and the reaction can be carried out by an ordinary heating method, or by radiating an ultrasonic wave, a microwave in a range of from 0.3 to 300 GHz or an electromagnetic wave around a microwave continuously or intermittently under controlled temperature. Removal of a hydrogen halide formed through the reaction outside the system is effective for accelerating the reaction, and an amine may be added to the reaction system for that purpose. Preferred examples of the amine include trietylamine. In the case where trietylamine is added, it is preferably used in an amount of 1 to 5 times by mole, more preferably from 2 to 3 times by mole, the α,α-dihaloamine. The reaction temperature varies depending on the structure of the substrate and cannot be determined unconditionally, but the reaction is completed quickly at a low temperature. In general, the reaction is preferably carried out at a temperature of 200° C. or less, and more preferably a temperature in a range of from room temperature to 150° C. The particularly preferred temperature is in a range of from 40 to 100° C. As the using amount of the substrate, 1 mol or more of the α,α-dihaloamine is preferably used per 1 mol of the aminoalcohol compound or the aminothiol compound, and the reaction may be carried out in a stoichiometrically excess or short amount. For example, in the case where the aminoalcohol compound or the aminothiol compound is used in a stoichiometrically excess amount, there is such an advantage in that the operation can be simplified upon separating and collecting the reaction product.

The reaction time of the reaction is preferably in a range of from 10 to 360 minutes for the ordinary thermal reaction. In the case where the reaction is carried out under radiation of an ultrasonic wave or a microwave, the reaction time is preferably from 0.1 to 180 minutes, and the radiation may be effected for a longer period of time. There is no necessity to use a solvent for carrying out the reaction, and a solvent may be used for effecting agitation sufficiently or for preventing the temperature from being increased. Preferred examples of the solvent include an aliphatic hydrocarbon, an aromatic hydrocarbon, a halogenated hydrocarbon, a halogenated aromatic hydrocarbon, a nitrile, an ether and the like, which are inert to the aminoalcohol or aminothiol and the α,α-dihaloamine as the substrate, and the reaction product, and the solvent may be used after appropriately selecting therefrom in combination.

After completing the reaction, the reaction product can be obtained by filtering the reaction liquid or filtering it after concentrating the solvent, or by an ordinary separation method, such as solvent extraction or the like. Depending on necessity, furthermore, a product having high purity can be obtained by applying a purifying method, such as column chromatography, recrystallization or the like.

EXAMPLE

The method of the present invention will be described in more detail with reference to the examples below. However, the present invention is not limited to the examples.

Example 1

Synthesis of 2-(3-methylphenyl)-2-oxazoline

2-Aminoethanol (2.4 mmol, 0.147 g), triethylamine (4 mmol, 0.202 g) and 4 mL of dichloromethane were placed in a 25-mL round-bottom flask, and 2 mL of a dichloromethane solution of N,N-diethyl-α,α-difluoro(3-methyl)benzylamine (which may be referred to as DFMBA, 2 mmol, 0.426 g) was added dropwise thereto under agitating at −20° C. over about 10 minutes. Thereafter, the temperature was increased to room temperature, and the reaction was carried out for 1 hour. After completing the reaction, the reaction mixed solution was neutralized by adding 10 mL of a saturated sodium hydrogen carbonate aqueous solution thereto. The solution was then extracted three times with 25 mL of diethyl ether, and the extract was dried with a suitable amount of potassium carbonate and was, after removing the solvent, purified by column chromatography. As a result, 2-(3-methylphenyl)-2-oxazoline (1.7 mmol, 0.274 g) as the target product was separated at a yield of 85%. The structural formula of the resulting product is shown below.

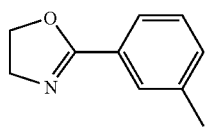

[ka 4]

Reference Example 1

Patent Document 1: German Patent No. 2,158,615

Synthesis of 2-(3-methylphenyl)-2-oxazoline

In Example 11 of the German patent, the isolation yield of 2-(3-methylphenyl)-2-oxazoline is 73%, which is obtained by reacting 1 mol of 3-methylbenzonitrile and 2 mol of 2-aminoethanol by using sodium acetate as a catalyst at 130° C. for 6 hours.

Example 2

Synthesis of 2-(3-methylphenyl)-2-oxazoline

The same procedures as in Example 1 were carried out except that triethylamine was not added, the reaction temperature was changed to 40° C. under dichloromethane reflux condition, and the reaction time was changed to 1 hour.

The isolation yield of 2-(3-methylphenyl)-2-oxazoline as a product was 83%.

Example 3

Synthesis of (4S)-2-(3-methylphenyl)-4-benzyl-2-oxazoline

The same procedures as in Example 2 were carried out except that (2S)-2-amino-3-phenylpropan-1-ol was used instead of 2-aminoethanol as a raw material.

The isolation yield of (4S)-2-(3-methylphenyl)-4-benzyl-2-oxazoline as a target product was 77%. The structural formula of the resulting product is shown below.

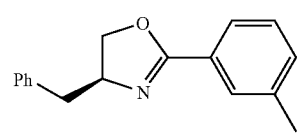

[ka 5]

Example 4

Synthesis of 2-(3-methylphenyl)-5-methyl-2-oxazoline

The same procedures as in Example 2 were carried out except that 1-aminopropan-2-ol was used instead of 2-aminoethanol as a raw material.

The isolation yield of 2-(3-methylphenyl)-5-methyl-2-oxazoline as a target product was 77%. The structural formula of the resulting product is shown below.

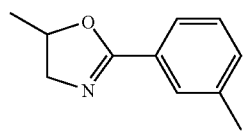

[ka 6]

Example 5

Synthesis of (4R)-2-(3-methylphenyl)-4-phenyl-2-oxazoline

The same procedures as in Example 2 were carried out except that 2-amino-2-phenylethanol was used instead of 2-aminoethanol as a raw material.

The isolation yield of (4R)-2-(3-methylphenyl)-4-phenyl-2-oxazoline as a target product was 77%. The structural formula of the resulting product is shown below.

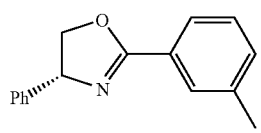

[ka 7]

Example 6

Synthesis of (4S)-2-(3-methylphenyl)-4-isobutyl-2-oxazoline

The same procedures as in Example 2 were carried out except that (2S)-2-amino-4-methylpentan-1-ol was used instead of 2-aminoethanol as a raw material.

The isolation yield of (4S)-2-(3-methylphenyl)-4-isobutyl-2-oxazoline as a target product was 68%. The structural formula of the resulting product is shown below.

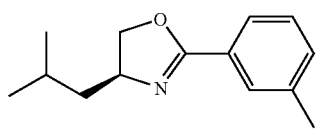

Example 7

Synthesis of 2-(3-methylphenyl)-4,4-dimethyl-2-oxazoline

The same procedures as in Example 1 were carried out except that 2-amino-2-methylpropan-1-ol was used instead of 2-aminoethanol as a raw material, and the reaction was carried out at 40° C.

The isolation yield of 2-(3-methylphenyl)-4,4-dimethyl-2-oxazoline as a target product was 59%. The structural formula of the resulting product is shown below.

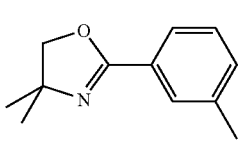

Example 8

Synthesis of (4R)-2-(3-methylphenyl)-4-methyl-2-oxazoline

The same procedures as in Example 2 were carried out except that (2R)-2-aminopropan-1-ol was used instead of 2-aminoethanol as a raw material.

The isolation yield of (4R)-2-(3-methylphenyl)-4-methyl-2-oxazoline as a target product was 42%. The structural formula of the resulting product is shown below.

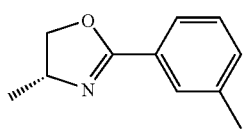

Example 9

Synthesis of (4S,5R)-ethyl 2-(3-methylphenyl)-5-methyl-2-oxazoline-4-carboxylate The same procedures as in Example 2 were carried out except that (2S,3R)-ethyl 2-amino-3-hydroxybutanoate was used instead of 2-aminoethanol as a raw material.

The isolation yield of (4S,5R)-ethyl 2-(3-methylphenyl)-5-methyl-2-oxazoline-4-carboxylate as a target product was 84%. The structural formula of the resulting product is shown below.

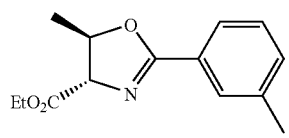

Example 10

Synthesis of (4S,5S)-ethyl 2-(3-methylphenyl)-5-methyl-2-oxazoline-4-carboxylate The same procedures as in Example 2 were carried out except that (2S,3R)-ethyl 2-benzamide-3-hydroxybutanoate was used instead of 2-aminoethanol as a raw material.

The isolation yield of (4S,5S)-ethyl 2-(3-methylphenyl)-5-methyl-2-oxazoline-4-carboxylate as a target product was 31%. The structural formula of the resulting product is shown below.

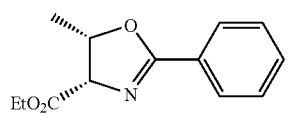

Example 11

Synthesis of (S)-methyl 2-(3-methylphenyl)-2-oxazoline-4-carboxylate

The same procedures as in Example 1 were carried out except that (S)-3-hydroxy-1-methoxy-1-oxopropane-2-aminium chloride was used instead of 2-aminoethanol as a raw material. The isolation yield of (S)-methyl 2-(3-methylphenyl)-2-oxazoline-4-carboxylate as a target product was 84%. The structural formula of the resulting product is shown below.

Example 12

Synthesis of (S)-ethyl 2-(3-methylphenyl)-2-thiazoline-4-carboxylate

The same procedures as in Example 1 were carried out except that (S)-3-mercapto-1-ethoxy-1-oxopropane-2-aminium chloride was used instead of 2-aminoethanol as a raw material. The isolation yield of (S)-ethyl 2-(3-methylphenyl)-2-thiazoline-4-carboxylate as a target product was 95%. The structural formula of the resulting product is shown below.

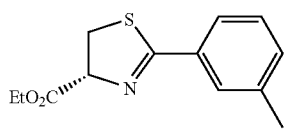

Example 13

Synthesis of 2-(3-methylphenyl)-benzoxazole

The same procedures as in Example 2 were carried out except that 2-aminophenol was used instead of 2-aminoethanol as a raw material, and the reaction was carried out at room temperature.

The isolation yield of 2-(3-methylphenyl)-benzoxazole as a target product was 90%. The structural formula of the resulting product is shown below.

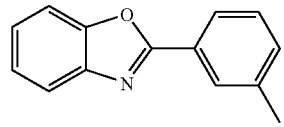

Example 14

Synthesis of 5,6-dihydro-2-(3-methylphenyl)-4H-[1,3]oxazine

The same procedures as in Example 1 were carried out except that 3-aminopropan-1-ol was used instead of 2-aminoethanol as a raw material, and the reaction was carried out at 80° C.

The isolation yield of 5,6-dihydro-2-(3-methylphenyl)-4H-[1,3]oxazine as a target product was 41%. The structural formula of the resulting product is shown below.

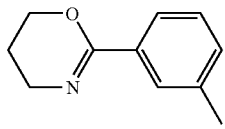

Example 15

Synthesis of 2-phenyl-2-oxazoline

The same procedures as in Example 1 were carried out except that 2.4 mmol of 2-aminoethanol was used as the aminoalcohol, and 2 mmol of N-(α,α-difluorobenzyl)pyrrolidine was used as the α,α-dihaloamine. As a result, the isolation yield of 2-phenyl-2-oxazoline as a target product was 72%.

Example 16

Synthesis of (4S)-2-phenyl-4-isobutyl-2-oxazoline

The same procedures as in Example 2 were carried out except that 2.4 mmol of (2S)-2-amino-4-methylpentan-1-ol was used as the aminoalcohol, and 2 mmol of N-(α,α-difluorobenzyl)pyrrolidine was used as the α,α-dihaloamine. As a result, the isolation yield of (4S)-2-phenyl-4-isobutyl-2-oxazoline as a target product was 74%.

Example 17

Synthesis of 2-phenyl-4,4-dimethyl-2-oxazoline

The same procedures as in Example 16 were carried out except that 2.4 mmol of 2-amino-2-methylpropan-1-ol was used as the aminoalcohol. As a result, the isolation yield of 2-phenyl-4,4-dimethyl-2-oxazoline as a target product was 41%.

Example 18

Synthesis of Benzoxazole

The same procedures as in Example 2 were carried out except that 2.4 mmol of 2-aminophenol was used as the aminoalcohol, and 2 mmol of N-difluoromethylmorpholine was used as the α,α-dihaloamine. As a result, the isolation yield of benzoxazole as a product was 50%.

Example 19

Synthesis of (4S,5R)-methyl 2-(4-methoxyphenyl)-5-methyl-2-oxazoline-4-carboxylate The same procedures as in Example 1 were carried out except that 2.4 mmol of (2S,3R)-methyl 2-amino-3-hydroxybutanoate was used as the aminoalcohol, and 2 mmol of N,N-diethyl-α,α-difluoro-(4-methoxy)benzylamine was used as the α,α-dihaloamine. As a result, the isolation yield of (4S,5R)-methyl 2-(4-methoxyphenyl)-5-methyl-2-oxazoline-4-carboxylate as a target product was 77%.

Example 20

Synthesis of (S)-methyl 2-(4-methoxyphenyl)-2-oxazoline-4-carboxylate

The same procedures as in Example 19 were carried out except that (S)-3-hydroxy-1-methoxy-1-oxopropane-2-aminium chloride was used as the aminoalcohol. As a result, the isolation yield of (S)-methyl 2-(4-methoxyphenyl)-2-oxazoline-4-carboxylate as a target product was 82%.

Example 21

Synthesis of 2-(3-methylphenyl)-2-oxazoline

The same procedures as in Example 1 were carried out except that 2.4 mmol of 2-aminoethanol was used as the aminoalcohol, and 2 mmol of N,N-diethyl-α-chloro-(3-methylphenyl)amidium chloride was used as the α,α-dihaloamine. As a result, the isolation yield of 2-(3-methylphenyl)-2-oxazoline as a target product was 82%.

It is apparent from the examples according to the present invention that a 2-oxazoline analogue and an oxazine analogue can be easily obtained under mild conditions of from room temperature to 40° C. According to the conventional art, for example, the isolation yield of 2-(3-methylphenyl)-2-oxazoline obtained under reaction conditions of 130° C. and 6 hours is 73% at most as shown in Reference Example 1. On the other hand, as shown in Example according to the present invention, the isolation yield of 2-(3-methylphenyl)-2-oxazoline obtained under reaction conditions of room temperature and 1 hour is 85%.

INDUSTRIAL APPLICABILITY

According to the present invention, a 2-oxazoline analogue or an oxazine analogue having an intended substituent, i.e., a 2-oxazoline compound, a 1,3-oxazine compound, a 2-thiazoline compound and a 1,3-thiazine compound, can be produced from a 1,2-aminoalcohol compound or a 1,2-aminothiol compound having various substituents and an α,α-dihaloamine compound under mild conditions in a simple manner, and can be widely used for medicines, agrochemicals, optical recording materials and the like.

The invention claimed is:

1. A method for producing a 2-oxazoline compound, a 2-thiazoline compound, a 1,3-oxazine compound or a 1,3-thiazine compound, represented by the formula (3), comprising reacting an amino compound represented by the formula (1) with an α,α-dihaloamine represented by the formula (2):

[ka 1]

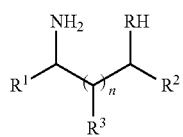

(1)

[ka 2]

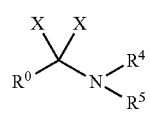

(2)

[ka 3]

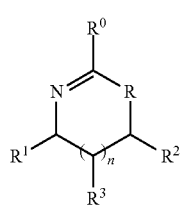

(3)

(in the formula (1) and the formula (3), n represents 0 or 1, and R represents an oxygen atom or a sulfur atom; in the formula (2), X represents a fluorine atom; in the formulae (1), (2) and (3), $R^1$, $R^2$ and $R^3$ each represents a hydrogen atom, an alkyl group, an aryl group, an aralkyl group or an alkoxycarbonyl group, and $R^4$ and $R^5$ each represents an alkyl group having 24 or less carbon atoms, an aryl group or an aralkyl group, and in the formulae (2) and (3), $R^0$ represents a phenyl group, a 2-methylphenyl group, a 3-methyl phenyl group, a 4-methylphenyl group, a 2-methoxyphenyl group or a 4-methoxyphenyl group; and $R^0$, $R^1$, $R^2$, $R^3$, $R^4$ and $R^5$ may be the same as or different from each other, and two or more of $R^1$, $R^2$ and $R^3$ or two or more of $R^0$, $R^4$ and $R^5$ may be bonded to each other to form a ring).

2. The method for producing a 2-oxazoline compound, a 2-thiazoline compound, a 1,3-oxazine compound or a 1,3-thiazine compound according to claim 1, wherein a 2-oxazoline compound represented by the formula (3), wherein n represents 0, and R represents an oxygen atom, is produced by reacting an aminoalcohol represented by the formula (1), wherein n represents 0, and R represents an oxygen atom, with an α,α-dihaloamine represented by the formula (2).

3. The method for producing a 2-oxazoline compound, a 2-thiazoline compound, a 1,3-oxazine compound or a 1,3-thiazine compound according to claim 1, wherein a 1,3-oxazine compound represented by the formula (3), wherein n represents 1, and R represents an oxygen atom, is produced by reacting an aminoalcohol represented by the formula (1), wherein n represents 1, and R represents an oxygen atom, with an α,α-dihaloamine represented by the formula (2).

4. The method for producing a 2-oxazoline compound, a 2-thiazoline compound, a 1,3-oxazine compound or a 1,3-thiazine compound according to claim 1, wherein a 2-thiazoline compound represented by the formula (3), wherein n represents 0, and R represents a sulfur atom, is produced by reacting an aminothiol represented by the formula (1), wherein n represents 0, and R represents a sulfur atom, with an α,α-dihaloamine represented by the formula (2).

5. The method for producing a 2-oxazoline compound, a 2-thiazoline compound, a 1,3-oxazine compound or a 1,3-thiazine compound according to claim 1, wherein a 1,3-thiazine compound represented by the formula (3), wherein n represents 1, and R represents a sulfur atom, is produced by reacting an aminothiol represented by the formula (1), wherein n represents 1, and R represents a sulfur atom, with an α,α-dihaloamine represented by the formula (2).

* * * * *